United States Patent [19]

Blum

[11] 4,227,413

[45] Oct. 14, 1980

[54] URINE SPECIMEN COLLECTOR

[76] Inventor: Alvin S. Blum, 2350 Del Mar Pl., Fort Lauderdale, Fla. 33301

[21] Appl. No.: 2,403

[22] Filed: Jan. 10, 1979

[51] Int. Cl.³ .............................................. G01N 1/18
[52] U.S. Cl. ............................. 73/421 R; 73/425.4 R
[58] Field of Search ................ 73/421 B, 421 R, 426, 73/425.4 R; 222/510, 469, 484

[56] References Cited

U.S. PATENT DOCUMENTS 2,667,075   1/1954   Blum ............................. 73/425.4 P

FOREIGN PATENT DOCUMENTS 103458   1/1966   Denmark ............................. 73/421 B
842069   6/1939   France ............................. 73/421 B Primary Examiner—Gerald Goldberg
Assistant Examiner—Denis E. Corr

[57] ABSTRACT

Improved apparatus for combined collection of an exact fraction of each of a plurality of urine voidings in a common storage container. Provision is made for dividing each voiding into a small aliquot portion and a balance portion further provision is made for storing a plurality of said aliquots in common storage; and for discarding said balance portion in a convenient fashion.

6 Claims, 5 Drawing Figures

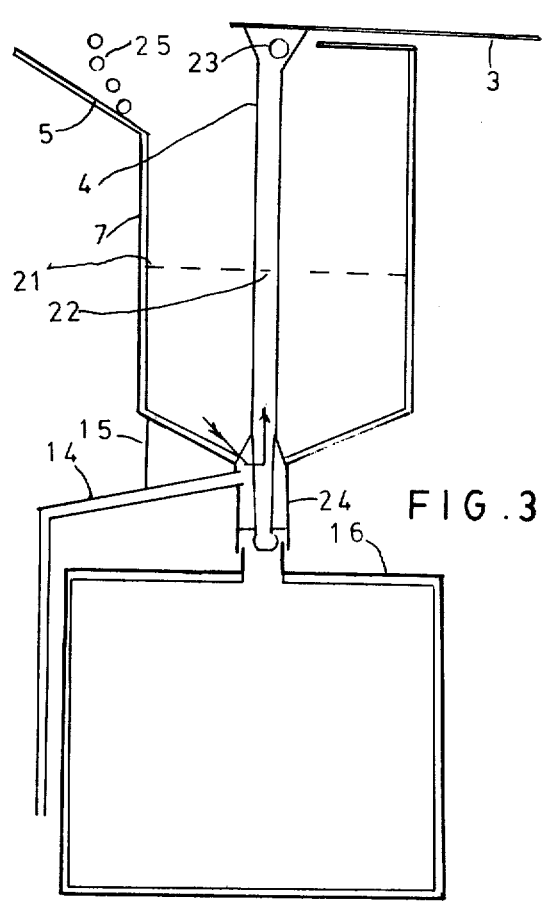
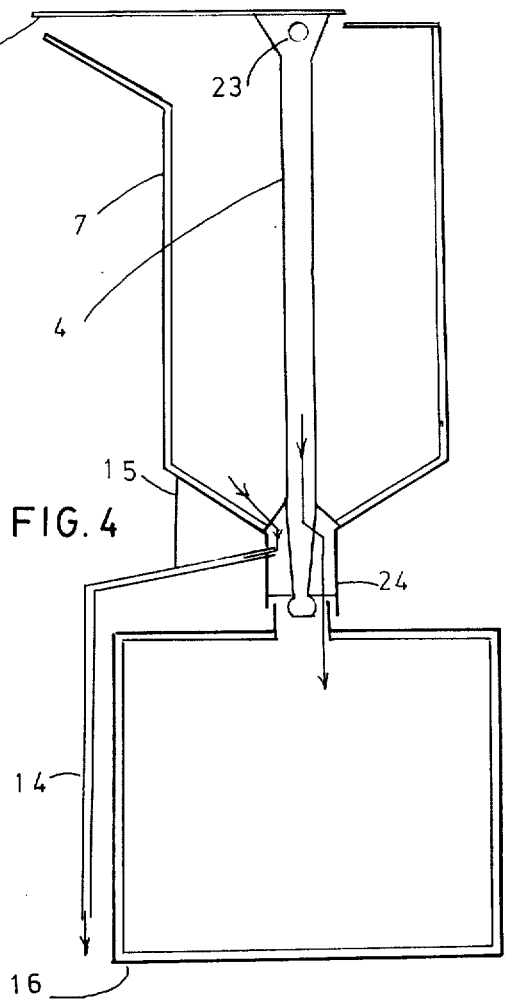
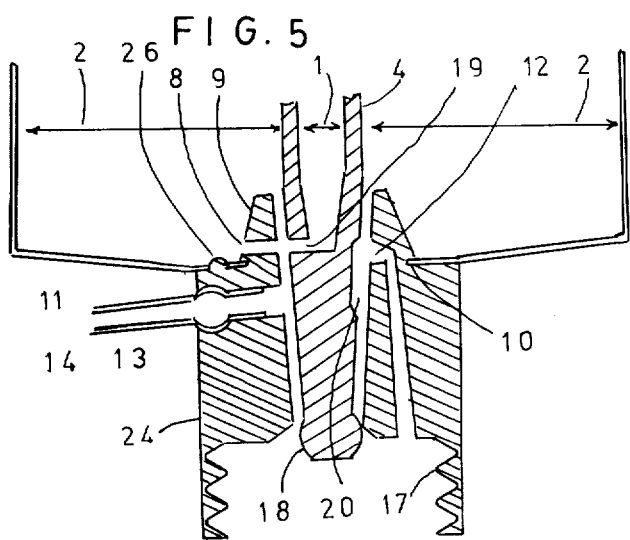
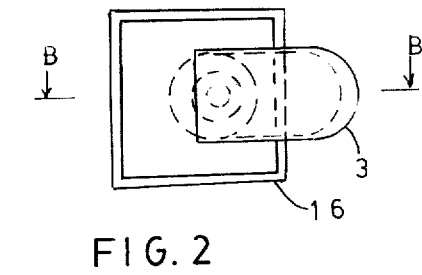
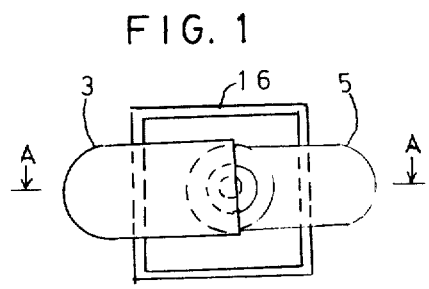

URINE SPECIMEN COLLECTOR

BACKGROUND OF THE INVENTION

1. Field of the Invention

This invention relates to urine specimen collecting apparatus.

2. Description of the Prior Art

The clinical laboratory is often called upon to measure the timed (24 hour for example) excretion of certain hormones, metabolites, drugs, etc. This requires collection of all urine passed in the interval. At the end of the interval, all the urine is mixed together, its total volume measured, and a smaller, representative portion (an aliquot) is dispensed for the actual analysis. Usually the urine must be stored refrigerated, often with an acid or other preservative. Because the analysis may be sensitive to interference by contaminants, very high purity reagents, water, and scrupulously clean glassware are required. In a 24 hour period urine volume may reach 10 liters when diuretics are used or fluids forced. This size container is awkward to store in the refrigerator, carry about, and urinate into directly for females. This often leads to supplying too small a container, which is then supplemented by any handy jar that is contaminated and has no preservative. Often the patient urinates into a more convenient but unclean receptacle and transfers it to the storage container. The presence of a corrosive preservative threatens the patient directly, contamination of the specimen threatens the patient indirectly by false results. U.S. Pat. No. 2,667,075 teaches proportional sampling with a device more awkward to use for this particular purpose.

SUMMARY OF THE PRESENT INVENTION

This invention provides a novel specimen handling apparatus for improving timed urine collection and analysis of urinary excretion of particular materials.

It is an object of the present invention to eliminate the need for storage and handling of large volumes of urine. It is another object of the invention to reduce contamination of specimens. It is a further object to promote more complete collection by providing convenient storage means. It is a further object to promote patient safety by isolating patient from preservatives in urine storage means. This invention takes advantage of the following observations:

1. Although large volumes of urine may be excreted in a 24 hour period, it is always divided into small increments, limited by the bladder capacity of approximately 0.4 liters.

2. Only a small fraction (aliquot) of the total mixed volume is actually used for analysis, the balance is discarded in the laboratory.

3. If one combines 1/20 portions of ten specimens the product will be identical to 1/20 of a pooled mixture of all ten specimens.

This apparatus takes an identical fixed fraction (aliquot) of each liquid specimen introduced and discards the remainder. It stores said aliquots in common storage means not in direct communication with inlet means, thereby protecting the user from contact with any preservatives that may be in common storage means. It is an object of the invention that the apparatus perform its functions so simply that many patients may be able to use the invention unaided. The foregoing and other objects of the present invention will be described more fully in the following more detailed description of the present invention.

BRIEF DESCRIPTION OF THE DRAWINGS

FIG. 1 shows a top view of a preferred embodiment of the invention with cover open.

FIG. 2 shows a top view with cover closed.

FIG. 3 shows a diagrammatic side view of a section on line A—A of FIG. 1.

FIG. 4 shows a diagrammatic side view of a section on line B—B of FIG. 2.

FIG. 5 shows a more detailed view of the valve portion of FIG. 3.

DESCRIPTION OF THE PREFERRED EMBODIMENT

This invention consists of two elongate containers concentrically mounted one within the other and sealably joined at their bases by valve means to form two chambers, an inner chamber and an outer annular chamber whose volumes have a discrete proportional relationship one to the other. Storage means are connected below valve means to receive proportional fractions of input liquid volumes from one chamber.

Referring first to top view of FIG. 1 and side view of FIG. 3, cover 3 is in open position exposing funnel like urine inlet 5 of outer chamber 7. Urine stream 25 is shown pouring into outer chamber 7. Cover 3 is attached to tube 4 the lower end of which is tapered and fits sealably in the tapered seat of valve body 24 so that tube 4 rotates between two functional valve positions as cover is rotated 180 degrees between open and closed positions. In the open position depicted in FIGS. 1,3,5, liquid level 22 inside tube 4 will be equal to liquid level 21 in surrounding chamber 7, because they communicate through hole 8 in valve body 24 and hole 19 in base of tube 4. Fluid communication is indicated by dotted line. The apparatus is so constructed that at every liquid level, cross sectional area 1 inside tube 4 is a constant fraction of cross sectional area 2 inside outer chamber 7. The result is that the volume of liquid contained within tube 4 is a constant fraction of the total liquid introduced. When cover 3 is rotated to the closed position of top view FIG. 2 and side view FIG. 4, tube 4 is rotated through 180 degrees and the liquid trapped within tube 4 runs down through hole 19 and hole 12 which are now aligned to form first outlet means connecting tube 4 to storage container 16. Hole 23 vents the tube. The aliquot of liquid drains through this first outlet means (dotted line) into storage container 16, which is generally large enough to contain all the aliquots normally expected in the collection period. Preservative is also stored in container 16 which fastens to molded valve body 24 by fastening means such as screw thread 17. Groove 20 in tapered base of tube 4 now connects hole 8 and hole 13 to form second outlet means connecting outer chamber 7 to waste, allowing the remainder of the specimen (dotted line) to drain out tube 14 to waste. Tube 14 is fastened to base of chamber 7 by fastening means 15. In another embodiment, not shown, tube 14 may enter a temporary waste chamber to hold residue for later emptying. Projection 26 of valve body 24 engages hole in base of chamber 7 preventing chamber 7 from rotating relative to valve body.

Valve body 24 is molded of a resilient lubricous material such as polyolefin. It snaps into base 11 of chamber 7 by inserting taper 9. Slot 10 causes valve body to lock and seal in place. Distension 18 at terminus of tube 4 causes taper to pull tightly and lock in place.

In operation, each voided specimen is treated alike. The cover is swung open so that the urine inlet is exposed. Patient voids in the opening. After voiding, user holds the device vertically over the toilet and closes the cover. This maneuver drains the aliquot through first outlet means into storage and the residue through second outlet means to waste. At the same time, the storage container is closed. Detents may indicate open and closed positions. In hospital an attendant may perform these duties after collection in another container. The result for a 1/20 aliquot collector might be: 1 ml. of preservative instead of 20 ml.; 0.9 liter container in the refrigerator instead of a 10 liter container; no larger volume graduates of urine to handle in the laboratory; less embarassment to the outpatient at work; and greater probability of a correct sample for analysis. In many cases the entire aliquot will be extracted for analysis so that no urine volume measurements would be required in the laboratory, and the result would simply be multiplied by twenty to yield total excretion. Inasmuch as the present invention is subject to many variations, modifications and changes in detail, it is intended that all matter described above or shown in the accompanying drawings be interpreted as illustrative and not in a limiting sense.

What is claimed is:

1. An aliquot sampling apparatus comprising: an outer elongate container having an upper inlet and a bottom outlet port; an inner elongate container spaced from the outer container and concentric therewith to provide an annular chamber therebetween, said inner container having a bottom access port; resilient sealing valve means at the bases of said containers and connected thereto, said resilient valve means snapped into the base of said outer container; first and second outlet means, said inner container being adjustable in said valve means to position said access port for communication with the outlet port of said outer container in a first position of said inner container; and to position said access port in communication with said first outlet means in a second position of said inner container, said second position also positioning the outlet port of said outer container in communication with said second outlet means.

2. The apparatus of claim 1 which further comprises storage means connected to said first outlet means for directly accumulating a plurality of aliquots dispensed from said inner container.

3. The apparatus of claim 1, which further comprises cover means for covering said containers, said cover means being connected to the inner container, thereby operatively controlling position of said inner container and said valve means when cover is moved from a first uncovered position to a second covered position.

4. The apparatus of claim 3 which further comprises detent means to more positively locate said first and second positions.

5. The apparatus of claim 1 wherein said inner and said outer containers are so constructed as to enclose cross sectional areas at every level which are in generally constant proportion to each other.

6. An automatic urine aliquot accumulating apparatus for collecting a known pooled fraction of a series of unknown volumes of liquid comprising: an outer elongate container having an upper inlet and a bottom outlet port; an inner elongate container spaced from the outer container and concentric therewith to provide an annular chamber therebetween, said inner container having a bottom access port, said inner and said outer containers so constructed as to enclose cross sectional areas at every level which are in generally constant proportion to each other; sealing valve means at the bases of said containers and connected thereto; first and second outlet means; said inner container being adjustable in said valve means to position said access port for communication with said outlet port of said outer container in a first position of said inner container; and to position said access port in communication with said first outlet means in a second position of said inner container, said second position also positioning the outlet port of said outer container in communication with said second outlet means; storage means connected to said first outlet means for accumulating a plurality of aliquots dispensed from said inner container; and cover means for covering said containers, said cover means being connected to said inner container, thereby operatively controlling position of said inner container and said valve means when cover is moved from a first uncovered position to a second covered position so that in said first uncovered position valve means is automatically in said first position and in said second covered position valve means is automatically in said second position without additional operator attention.

* * * * *